United States Patent [19]

Ptchelintsev et al.

[11] Patent Number: 5,932,229
[45] Date of Patent: *Aug. 3, 1999

[54] OXA DIACIDS AND RELATED COMPOUNDS FOR TREATING SKIN CONDITIONS

[75] Inventors: Dmitri Ptchelintsev, Mahwah; Neil Scancarella, Wyckoff; Robert Kalafsky, Ogdensburg, all of N.J.

[73] Assignee: Avon Products, Inc., New York, N.Y.

[ * ] Notice: This patent is subject to a terminal disclaimer.

[21] Appl. No.: 08/850,333

[22] Filed: May 2, 1997

Related U.S. Application Data

[63] Continuation-in-part of application No. 08/636,540, Apr. 25, 1996, Pat. No. 5,834,513.

[51] Int. Cl.⁶ .................................................... A61K 7/48
[52] U.S. Cl. .................... 424/401; 424/61; 424/701; 424/73; 424/443; 424/DIG. 5; 514/532; 514/533; 514/546; 514/547; 514/550; 514/551; 514/552; 514/557; 514/561; 514/562; 514/563; 514/564; 514/566; 514/568; 514/572; 514/574; 514/578; 514/625; 514/626; 514/844; 514/846; 514/859; 514/861; 514/863; 514/880; 514/881; 514/937; 514/938; 514/944
[58] Field of Search ................................ 424/401, DIG. 5, 424/61, 701, 447, 93; 514/532, 533, 546, 547, 550, 551, 552, 557, 563, 564, 506, 568, 572, 574, 578, 561, 562, 625, 626, 844, 846, 859, 861, 863, 850, 851, 937–938, 944

[56] References Cited

U.S. PATENT DOCUMENTS

| | | | |
|---|---|---|---|
| 4,136,098 | 1/1979 | Burzin et al. | 260/343 |
| 4,153,726 | 5/1979 | Borggrefe et al. | 424/313 |
| 4,292,326 | 9/1981 | Nazzaro-Porro | 424/317 |
| 4,386,104 | 5/1983 | Nazzaro-Porro | 424/317 |
| 4,721,579 | 1/1988 | Kim | 252/79 |
| 4,885,282 | 12/1989 | Thornfeldt | 514/53 |
| 4,916,206 | 4/1990 | Day et al. | 528/272 |
| 5,008,443 | 4/1991 | Day et al. | 560/169 |
| 5,017,675 | 5/1991 | Marten et al. | 528/111 |
| 5,087,440 | 2/1992 | Cacheris et al. | 424/9 |
| 5,091,171 | 2/1992 | Yu et al. | 424/642 |
| 5,098,692 | 3/1992 | Gries et al. | 424/9 |
| 5,108,751 | 4/1992 | Hagan et al. | 424/401 |
| 5,319,004 | 6/1994 | Marten et al. | 523/404 |
| 5,385,943 | 1/1995 | Nazzaro-Porro | 514/574 |
| 5,464,929 | 11/1995 | Bezwada et al. | 528/361 |
| 5,834,513 | 11/1998 | Ptchelintsev et al. | 514/561 |
| 5,847,003 | 12/1998 | Ptchelintsev et al. | 514/532 |
| B1 5,091,171 | 9/1995 | Yu et al. | 424/642 |

FOREIGN PATENT DOCUMENTS

| | | |
|---|---|---|
| 2404047 | 8/1975 | Germany . |
| 29 36 123 A1 | 4/1981 | Germany . |
| 62-149797 | 7/1987 | Japan . |
| 3-170410 | 7/1991 | Japan . |
| 7-304653 | 11/1995 | Japan . |

OTHER PUBLICATIONS

English translation of the specification of Japanese Patent No. 07–304,653.
English translation of the specification of Japanese Patent No. 03–170,410.
English translation of the specification of Japanese Patent No. 62–149,797.
HCAPLUS 1996:91910, abstract of JP–07–304652, 1995.
HCAPLUS 1996:87739, abstract of JP 07–304653, 1995.
HCAPLUS 1992:433416, abstract of JP 03–170410, 1991.
HCAPLUS 1996:639304, abstract of JP 02–258708, 1990.
HCAPLUS 1989:636316, abstract of JP 63–280008, 1988.
HCAPLUS 1989:601377, abstract of JP 63–80798, 1988.
HCAPLUS 1988:187489, abstract of US Patent #4,721,579 which is enclosed.
HCAPLUS 1987:604947, abstract of JP 62–149797, 1987.
HCAPLUS 1987:119294, abstract of DE 3618725, 1987.
HCAPLUS 1975:609328, abstract of DE 2404047, 1975.
Merck Index, Compound No. 2477 (Esterified Estrogens), 1983.

*Primary Examiner*—Jyothsna Venkat
*Attorney, Agent, or Firm*—Ohlandt, Greeley, Ruggiero & Perle, L.L.P.

[57] ABSTRACT

Described are the use of compounds of Formula (I), depicted below, as active principals for treating skin conditions; compositions containing these compounds; and methods of treating skin conditions using these compounds and compositions.

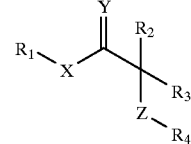

(I)

wherein $R_4$ is $(CR_5R_6-CR_7R_8-X_1)_n -CR_9R_{10}-C(=X_2)X_3R_{11}$, n is an integer from 1 to 18; $R_1$, $R_2$, $R_3$, $R_5$, $R_6$, $R_7$, $R_8$, $R_9$, $R_{10}$ and $R_{11}$, are independently, hydrogen or non-hydrogen substituents; and X, $X_1$, $X_2$, $X_3$, Y and Z are independently, O, NH, or S.

32 Claims, No Drawings

OXA DIACIDS AND RELATED COMPOUNDS FOR TREATING SKIN CONDITIONS

RELATED APPLICATION

This application is a continuation-in-part of application Ser. No. 08/636,540, filed Apr. 25, 1996, now U.S. Pat. No. 5,834,513.

BACKGROUND OF THE INVENTION

I. Field of Invention

The present invention relates to a new class of compounds for use as active principals for topical treatment of skin conditions, to compositions containing these compounds and to methods of treating skin conditions using these compounds and compositions. Compounds of the class include those of Formula (I)

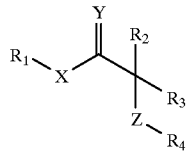

(I)

wherein, $R_4$ is $(CR_5R_6—CR_7R_8—X_1)_n—CR_9R_{10}—C(=X_2)X_3R_{11}$; n is an integer from 1 to 18; $R_1$, $R_2$, $R_3$, $R_5$, $R_6$, $R_7$, $R_8$, $R_9$, $R_{10}$ and $R_{11}$, are independently hydrogen or non-hydrogen substituents, with preferred non-hydrogen substituents including alkyls, alkenyls, oxa-alkyls, aralkyls and aryls; and X, $X_1$, $X_2$, $X_3$, Y and Z are independently, O, NH or S, with preferred compounds including those in which X, $X_1$, $X_2$, $X_3$, Y and Z are each oxygen and $R_1$, $R_2$, $R_3$, $R_5$, $R_6$, $R_7$, $R_8$, $R_9$, $R_{10}$ and $R_{11}$, are each hydrogen.

II. Description of the Prior Art

Dermal use of alpha hydroxyacids having an all carbon backbone is described in U.S. Pat. No. 5,091,171. Cosmetic compositions using 2-hydroxyalkenoic acid are disclosed, for example, in U.S. Pat. No. 5,108,751. Such compounds must have an unsubstituted alpha hydoxy group on a carbon backbone and are purportedly used to impart beneficial effects to the skin. However, the trend is away from the use of such alpha hydroxyacids since they necessitate low operational pH ranges that for the most common forms, i.e. glycolic and lactic acids, are known to cause skin irritations.

Topical formulations comprising straight, all carbon backbone, dicarboxylic acids have been proposed as replacements for alpha hydroxyacids. For example, U.S. Pat. Nos. 4,292,326, 4,386,104 and 5,385,943 describe the use of dicarboxylic acids having 7 to 13 carbon atoms for various skin indications. Similarly, U.S. Pat. No. 4,885,282 states that a 4 to 18 carbon dicarboxylic acid compound is useful for the treatment of skin disorders.

The problem with the use of these dicarboxylic acids is their inherent insolubility in aqueous solutions. Such solutions make up the majority of cosmetic delivery systems. Also, dicarboxylic acids that have all carbon backbones are solid at ambient temperatures, extremely difficult to work with and, if a solution is achieved, the result is an aesthetically unpleasant mixture unsuitable for cosmetic use.

Therefore, there is a need for a compound or class of compounds that can be used as mild, exfoliating actives for topical treatment of skin.

There is also a need for a mild, exfoliating topical composition that contains a water soluble compound that can be manufactured into an aesthetically acceptable cosmetic or dermatologic products.

SUMMARY OF THE INVENTION

It is an object of the present invention to provide a water soluble compound or class of such compounds that can be manufactured into an aesthetically acceptable, mild, exfoliating composition for topical use.

It is another object of the present invention to provide topical compositions with multiple skin care benefits.

It is a further object of the present invention to provide a new, dermatologic and cosmetic use for oxa diacids.

These and other objects will become evident from the following disclosure.

DETAILED DESCRIPTION OF THE INVENTION

The basic compound of this invention is a compound of the following Formula (I):

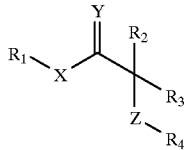

wherein, $R_4$ is $(CR_5R_6—CR_7R_8—X_1)_n—CR_9R_{10}—C(=X_2)X_3R_{11}$; n is an integer from 1 to 18; $R_1$, $R_2$, $R_3$, $R_5$, $R_6$, $R_7$, $R_8$, $R_9$, $R_{10}$ and $R_{11}$, are independently hydrogen or non-hydrogen substituents.

X, $X_1$, $X_2$, $X_3$, Y and Z are independently, O, NH, or S. Preferred are those compounds in which X, $X_1$, $X_2$, $X_3$, Y and Z are all oxygen. Most preferred are those compounds in which X, $X_1$, $X_2$, $X_3$, Y and Z are each oxygen, and $R_1$, $R_2$, $R_3$, $R_5$, $R_6$, $R_7$, $R_8$, $R_9$, $R_{10}$ and $R_{11}$, are each hydrogen.

The preferred non-hydrogen substituents include alkyls alkenyls, oxa-alkyls, aralkyls and aryls. Examples of non-hydrogen substituents include methyl, ethyl, propyl, isopropyl, butyl, isobutyl, hexyl, heptyl, octyl, nonyl, dodecanyl, methoxy, ethoxy, propoxy, butoxy, cyclohexenyl, hydroxymethyl, hydroxyethyl, hydroxypropyl, cyclobutyl and cyclohexanyl.

Exemplary compounds of Formula (I) include 3,6-dioxaoctadioic acid (HOOC—$CH_2$—O—$CH_2$—$CH_2$—O—$CH_2$—COOH); 3,6,9-trioxaundecane-dioic acid (HOOC—$CH_2$—O—$CH_2$—$CH_2$—O—$CH_2$—$CH_2$—O—$CH_2$—COOH); 3,6,9,12-tetraoxatetradecanedioic acid (HOOC—$CH_2$—O—$CH_2$—$CH_2$—O—$CH_2$—$CH_2$—O—$CH_2$—$CH_2$—O—$CH_2$—COOH); 3,6,9,12,15-pentaoxa-heptadecanedioic acid (HOOC—$CH_2$—O—CHz—$CH_2$—O—$CH_2$—$CH_2$—O—$CH_2$—$CH_2$—O—$CH_2$—$CH_2$—O—$CH_2$—COOH); 2-methyl-3,6,9-trioxaundecanedioic acid (HOOC—$CH_2$—O—$CH_2$—$CH_2$—O—$CH_2$—$CH_2$—O—CH($CH_3$)—COOH); 2-ethyl-3,6,9,12-tetraoxatetradecane-dioic acid (HOOC—$CH_2$—O—$CH_2$—$CH_2$—O—$CH_2$—$CH_2$—O—$CH_2$—$CH_2$—O—CH ($C_2H_5$)—COOH); 2-phenyl-3,6,9-trioxaundecanedioic acid (HOOC—CH (Ar)—O—$CH_2$—$CH_2$—O—$CH_2$— $CH_2$—O—$CH_2$—COOH); 3,6,9-trioxaun-decanedioic acid diethyl ester ($H_2C_2$—OOC—$CH_2$—O—$CH_2$—$CH_2$—O—$CH_2$—$CH_2$—O—$CH_2$—COO—$C_2H_5$); 3,6,9-triaminoun-decanedioic acid (HOOC—$CH_2$—NH—$CH_2$—$CH_2$—NH—$CH_2$—$CH_2$—NH—$CH_2$—COOH); 3,6,9,12-tetraminotetra-decanedioic acid (HOOC-$CH_2$—NH—$CH_2$—$CH_2$—NH—$CH_2$—$CH_2$—NH—$CH_2$—$CH_2$—NH—$CH_2$—COOH); 3-amino-6,9-dioxaundecanedioic acid (HOOC—$CH_2$—NH—$CH_2$—$CH_2$—O—$CH_2$—$CH_2$—O—$CH_2$—COOH);

3,6-diamino-9-oxaundecanedioic acid (HOOC—$CH_2$—NH—$CH_2$—$CH_2$—NH—$CH_2$—$CH_2$—O—$CH_2$—COOH); 3,6,9-trithioundecanedioic acid (HOOC—$CH_2$—S—$CH_2$—$CH_2$—S—$CH_2$—$CH_2$—S—$CH_2$—COOH); 3,6-dithio-9,12-dioxatetradecanedioic acid (HOOC—$CH_2$—S—$CH_2$—$CH_2$—S—$CH_2$—$CH_2$—O—$CH_2$—$CH_2$—O—$CH_2$—COOH); 3-amino-6,9-dioxaundecanedioic acid monoamide (HOOC—$CH_2$—NH—$CH_2$—$CH_2$—O—$CH_2$—$CH_2$—O—$CH_2$—CO—$NH_2$); 3-amino-6,9-dioxa-undecane-dioic acid diamide ($H_2N$—OC—$CH_2$—NH—$CH_2$—$CH_2$—O—$CH_2$—$H_2$—O—$CH_2$—$CONH_2$); 3,6,9-trioxaundecanedioic acid monoamide (HOOC—$CH_2$—O—$CH_2$—$CH_2$—O—$CH_2$—$CH_2$—O—$CH_2$—$CONH_2$); 3,6,9-trioxaundecanedioic acid diamide ($H_2NOC$—$CH_2$—O—$CH_2$—$CH_2$—O—$CH_2$—$CH_2$—O—$CH_2$—$CONH_2$); 2-10-dimethyl-3,6,9-trioxa-undecanedioic acid (HOOC—CH—($CH_3$)—O—$CH_2$—$CH_2$—O—$CH_2$—$CH_2$—O—CH($CH_3$)—COOH); and 2,10-dimethyl-3,9-dithio-6-oxaundecanedioic acid (HOOC—CH($CH_3$)—S—$CH_2$—$CH_2$—O—$CH_2$—$CH_2$—S—CH($CH_3$)—COOH).

Compounds of Formula (I) are described as intermediates useful in the making of curing agents and hardeners for epoxy resins in U.S. Pat. Nos. 5,017,675 and 5,319,004, both assigned to Hoechst AG. German Published Application No. DE-A-2936123 describes the preparation of such epoxy resin intermediate compounds. Such compounds are also commercially available from Hoechst AG.

Compounds of Formula I can also be prepared from commercially available polamines, polyols and polythiols by routine chemical reactions well known to those skilled in the art such as amidation, catalytic oxidation, esterification and other well known organic chemistry synthetic protocols, as described in organic chemistry textbooks including March, *Advanced Organic Chemistry: Reactions, Mechanisms, and Structure,* 3rd ed., John Wiley Interscience (1985) and Carey et al. *Advanced Organic Chemistry,* 3rd ed., Parts A and B, Plenum Press, New York (1990).

The oxa compounds useful in the topical compositions of this invention can also be in the form of derivatives that are converted back to an acidic form by action of hydrolytic enzymes in the skin such as glycosidases, phosphatases, esterases and amidases. Examples of suitable derivatives include esters of Formula I compounds with aliphatic alcohols, carbohydrates, amides, lactones and anhydrides.

As defined herein, all compounds of Formula (I), and derivatives thereof, will be referred to collectively as "oxa diacids" and/or "oxa compounds" and/or "oxa diacid compounds".

A "topical application" refers to spreading or laying directly onto the surface of skin. A "topical composition" refers to a composition intended to be directly layed onto or spread on the surface of skin. An "effective amount" means an amount of a compound or a composition sufficient to induce a positive change (e.g. normalization of desquamation) in the skin condition to be treated such as those attributed to, accompanied or exacerbated by abnormal desquamation. A "physiologically acceptable vehicle" or a "suitable topical vehicle" refers to drugs, cosmetics, medicaments or inert ingredients that are suitable for use in direct contact with human tissues without undue toxicity. All percentages refer to weight percent, based on the total weight of the topical composition.

In accordance with the invention, oxa compounds are used as active principals in topical applications to treat various skin conditions attributed to, accompanied by or exacerbated by abnormal desquamation. Such conditions include, but are not limited to, dry skin, ichthyosis, palmar and plantar hyperkeratoses, dandruff, lichen simplex chronicus, Dariers disease, keratoses, lentigines, age spots, melasmas, blemished skin, acne, psoriasis, eczema, pruritis, inflammatory dermatoses, striae distensae (i.e. stretch marks), warts and calluses.

The compounds are unexpectedly and surprisingly found to be useful as active agents in topical preparations for treating signs of dermatological aging, both photoaging and intrinsic aging, including skin wrinkles such as fine wrinkling in the eye area or "crows feet" or fine wrinkles around the mouth area, irregular pigmentation, sallowness, loss of skin resilience and elasticity.

Oxa compounds and topical compositions containing them are also useful for treating disorders associated with the nails, cuticles and hair such as ingrown hair, folliculitis and Pseudofolliculitis barbae. The present compounds also soften hair and promote the elimination of hair ingrowths, making the compounds of Formula (I) useful in shaving compositions.

The oxa compounds can be incorporated into the compositions as free acids or as corresponding salts derived by neutralization with organic or inorganic bases such as triethanolamine, arginine, lysine, potassium hydroxide, sodium hydroxide, lithium hydroxide, ammonium hydroxide.

When used in combination with a physiologically acceptable vehicle to form a topical composition, the effective amount of the oxa compound can be within the range from about 0.1% to about 95%. Both the effective amount and the frequency of application will vary depending on the particular skin condition treated, the age and physical condition of the person under treatment, the severity of the condition, the duration of treatment, the nature of concurrent treatments, the specific compound or compositions employed, the particular vehicle utilized to deliver the compound or compositions, and other like factors within the knowledge and expertise of those skilled in the art.

The efficacy of the oxa compounds in treating skin conditions has been found to be affected by the pH of the composition. It is believed desirable to maintain the pH of the composition in the acid range pH<7.0, preferably pH<5.0, most preferably in the pH range between 3.5 and 4.0. The pH of the composition can be adjusted by adding water soluble salts formed by strong bases (e.g. KOH, NaOH, NHOH) and weak acids (e.g. phosphoric acid, acetic acid, lactic acid, carbonic acid). Examples of such salts include potassium biphosphate, sodium phosphate, sodium acetate, sodium lactate and the like. Other methods useful for adjusting the pH of topical compositions are known to those skilled in the art.

Compositions of the present invention have clear advantages over alpha hydroxyacid formulations, including superior mildness. Formulations containing alpha hydroxyacids, such as glycolic and lactic acids, can cause substantial discomfort to some individuals and symptoms of severe skin irritation in others, upon facial application. For instance, a formulation containing 4.0% glycolic acid at pH 3.7 produced a skin irritation (PII) score of 0.23 when tested on 20 panelists. In contrast, a composition containing 10% of 3,6, trioxaundecanedioic acid at pH 3.7 produced a PII score of only 0.13 (see Example 2, below).

Compositions that manifest a PII score of less than or equal to 0.15 are considered non-irritating; those exhibiting PII scores between 0.15 and 0.3 are considered moderately irritating; and compositions that elicit a PII score of more than 3.0 from tested panelists are considered serious irritants. The PII scoring takes into consideration such factors as the number of panelists displaying irritation symptoms compared to the total number of panelists in the test.

While being significantly gentler to skin than glycolic acid formulations, the oxa diacid compositions of the present invention are highly effective in normalizing the desquamation of the upper stratum corneum, an activity required for the alleviation of the skin conditions listed above.

The topical compositions of the present invention also have advantages over compositions containing dicarboxylic acids including better water solubility and superior stratum corneum desquamatory activity.

Oxa diacids easily dissolve in water to concentrations of at least 20 to 30% by weight and, therefore, allow a much wider range of composition flexibility.

Dicarboxylic acids of moderate to long chain length, which have straight, all-carbon backbones, are virtually insoluble in water and other aesthetically acceptable vehicle. This severely limits the choice of delivery vehicles for the dicarboxylic acids. The desquamatory activity of such dicarboxylic acids is also questionable. For example, formulations containing 5% and 10% dodecanedioic acid do not produce any normalizing effect on stratum corneum desquamation beyond that of its vehicle alone.

Some specific examples of vehicles found to be suitable for use with the oxa compounds include;

(1)(a) about 2 wt % to about 10 wt % glycerin, (b) about 1 wt % to about 10 wt % propylene glycol, (c) about 0.1 wt % to about 2 wt % hydroxyethyl cellulose, (d) about 0.1 wt % to about 1 wt % imidazolidilyl urea, and (e) about 0.01 wt % to about 2 wt % disodium-EDTA;

(2) (a) about 1 wt % to about 10 wt % glycerin, (b) about 1 wt % to about 10 wt % propylene glycol, (c) about 1 wt % to about 10 wt % octyl palmitate, (d) about 1 wt % to about 10 wt % myristyl myristate, (e) about 1 wt % to about 6 wt % cetearyl alcohol/ Ceteareth-20, (f) about 0.5 wt % to about 6 wt % glyceryl monostearate, (g) about 0.1 wt % to about 2 wt % hydroxyethyl cellulose, (h) about 0.1 wt % to about 1 wt % imidazolidilyl urea, about 0.05 wt % to about 0.5 wt % methyl paraben, and (J) about 0.01 wt % to about 2 wt % disodium-EDTA; and (3)(a) about 2 wt % to about 10 wt % glycerin, (b) about 1 wt % to about 10 wt % octyl palmitate, (c) about 1 wt % to about 10 wt % myristyl myristate, (d) about 1 wt % to about 7 wt % cetearyl alcohol/ Ceteareth-20, (e) about 1 wt % to about 10 wt % propylene glycol, (f) about 1 wt % to about 6 wt % glyceryl monostearate, (g) about 0.1 wt % to about 2 wt % hydroxyethyl cellulose, (h) about 0.1 wt % to about 1 wt % imidazolidilyl urea, (i) about 0.05 wt % to about 0.5 wt % methyl paraben, and (j) about 0.01 wt % to about 2 wt % disodium-EDTA.

The topical compositions of the present invention can be made as lotions. A first or more basic lotion comprises about 0.1 to about 90%, preferably from about 1 to about 50%, and most preferably about 5 to about 20% of the oxa diacid, and the remainder water. A second lotion has about 0.1 to about 90%, preferably from about 1 to about 50%, and most preferably about 5 to about 20% of the oxa diacid, about 0.5 to about 50% of an emollient about 0.1 to about 30% of an emulsifier and the remainder water. The second lotion may also contain up to about 10% of a preservative, from about 0.1 to about 3% of a fragrance, and up to about 5% of a dye or a pigment.

The topical composition of the invention can also be formulated as a cream. A first or more basic cream comprises about 0.1 to about 95%, preferably from about 1 to about 50%, and most preferably about 5 to about 20% of the oxa diacid, from about 0.5 to about 50% of an emollient, about 0.1 to about 6% of a thickener and the remainder water. A second, preferred cream comprises about 0.1 to about 90%, preferably from about 1 to about 50%, and most preferably about 5 to about 20% of the oxa diacid, from about 0.5 to about 50% of an emollient, about 0.1 to about 30% of an emulsifier, about 0.1 to about 6% of a thickener and the remainder water.

The oxa diacid can be combined with most conventional emollients including mineral oil, petrolatum, paraffin, ceresin, ozokerite, microcrystraline wax, perhydrosqualene dimethyl polysiloxanes, methylphenyl polysiloxanes, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids. Other suitable emollients can be found in Sagarin, *Cosmetics, Science and Technology,* 2nd Ed., vol. 1, pp. 32–43 (1972), the contents of which are incorporated herein by reference.

The emulsifiers that can be cationic, anionic, nonionic, amphoteric, or a combination thereof. Nonionic emulsifiers are preferred. Exemplary nonionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isothionates. Other suitable emulsifiers can be found in McCutcheon, *Detergents and Emulsifiers,* North American Edition, pp. 317–324 (1986), the contents of which are incorporated herein by reference.

The preservatives suitable for use with the present compositions include alkanols, especially ethanol and benzyl alcohol, parabens, sorbates, urea derivatves, and isothiazolinones.

While such lotions or creams can be made using conventional homogenization methods known to those skilled in the art, it is also possible to use a process of microfluidization that involves co-mixing the aqueous phase and the oil phase of such creams and lotions in a high-pressure homogenizer that reduces the emulsion particle size dramatically to about $\frac{1}{400}$th the size of those in creams and lotions prepared without applying high pressure. Microfluidization allows one to prepare elegant stable creams and lotions containing effective amounts of an oxa diacid without the use of traditional emulsifiers and surfactants.

The topical compositions of the invention can also be formulated as a micro-emulsion. A first, basic microemulsion system comprises about 0.1 to about 50%, preferably from about 1 to about 30%, and most preferably about 5 to about 20% of the oxa diacid, from about 0.5 to about 20% of a hydrocarbon, from about 0.5 to about 20% of an oil, and the remainder water. A second, more preferred micro-emulsion system comprises about 1 to about 20% of the oxa diacid, from about 0.5 to about 15% of a hydrocarbon, from about 1 to about 15% of an oil, from about 0.1 to about 10% of a fatty alcohol, up to 30% of an nonionic surfactant, and the remainder water.

The topical compositions of the invention can be formulated as oil-in-water or water-in-oil emulsions, gels, lotions, ointments, sticks, sprays, tapes, patches. The inventive compositions can also be in the form of a multiphase emulsion, such as a water-in-oil-in-water type emulsion as disclosed in U.S. Pat. No. 4,254,105, incorporated herein by reference. The compositions of the invention can also be formulated as triple emulsions of the oil-in-water-silicone fluid type disclosed in U.S. Pat. No. 4,960,764, incorporated herein by reference.

The compositions of the invention can also be made as a liposomal formulation, for example, according to the methods d scribed in Mezei, *J. Pharmaceut. Pharmacol.,* vol. 34, pp. 473–474 (1982), or modification thereof. In such compositions, droplets of the oxa diacid solution can be entrapped inside the liposomal vesicles with the shell of the liposome being a phospholipid or other suitable lipids (e.g. skin lipids). To form a topical composition, the liposomes can then be added to any of the carrier systems described above according, for example, to the preparation modes, uses and compositions of topical liposomes described in Mezei, *Topics in Pharmaceutical Sciences,* Breimer et al. Eds., pp. 345–358, Elsevier Science Publishers BV, New York (1985), incorporated herein by reference, or according to the reverse-phase evaporation method described in Szoka et al., *Proc. Nat. Acad. Sciences,* vol. 75, pp. 4194–4198 (1978), and Diploses et al., *J. Soc. Cosmetic Chemists,* vol. 43, pp93–100 (1992), each of which is incorporated herein by reference. Solutions of oxa diacids can also be entrapped in polymeric vesicles with a shell consisting of a suitable polymeric material such as gelatin, cross-linked gelatin, polyamide, poylacrylates and the like to form a vesicle that is then incorporated into the topical composition.

The compositions of the invention can include only an oxa compound as an active ingredient, or can use the oxa compound in combinations with other cosmetic and pharmaceutical actives and excipients. Suitable other cosmetic and pharmaceutical agents include, but are not limited to, antifungals, vitamins, sunscreens, retinoids, antiallergenic agents, depigmenting agents, anti-inflammatory agents, anesthetics, surfactants, moisturizers, exfolients, stabilizers, preservatives, antiseptics, thickeners lubricants, humectants, chelating agents and skin penetration enhancers, as well as the emulsifiers, emollients, fragrances and colorants discussed above.

Examples of suitable thickening agents include xanthan gum, xanthan gum brine tolerant, hydroxypropyl cellulose, hydroxyethyl cellulose, carbopol and gum acacia, polyacrylamide isoparaffin emulsion (available from Seppic Co. under the tradename SEPPIGEL 305), vee-gum or magnesium aluminum silicate.

In topical compositions, oxa diacids are also compatible with, and their utility can be enhanced by, humectants, such as urea, PCA, amino acids, certain polyols and other compounds with hygroscopic properties.

Topical compositions can also be formed to contain about about 0.1 to about 90%, preferably from about 1 to about 50%, and most preferably about 5 to about 20% of the oxa diacid, in combination with a keratolytic agent, such as salicylic acid and benzoyl peroxide, and skin lightening agents such as kojic acid benzoquinone, licorice derivatives, ascorbic acid and its derivatives (e.g. magnesium ascorbyl phosphate), and glycerhetinic acid and its derivatives.

From about 0.1 to about 90%, preferably from about 1 to about 50%, and most preferably about 5 to about 20% of the oxa diacid can be used to form a topical formulation in combination with organic and inorganic sunscreens such as titanium dioxide, zinc oxide, benzylidene camphor, anthranilates, butylmethoxydibenzoylmethane, naphtholsulphonates and cinnamic acid derivatives Of these, butylmethoxydibenzoylmethane and cinnamic acid derivatives are preferred.

Topical compositions of the invention can also contain about 0.1 to about 90%, preferably from about 1 to about 50%, and most preferably about 5 to about 20% of the oxa diacids co-formulated with (i) retinoids such as retinol, retinoic acid, retinyl palmitate, retinyl propionate, retinyl acetate, isotretinoin as well as synthetic retinoid mimics; (ii) hormonal compounds such as estriol, estradiol, estrone or conjugated estrogens; (iii) alpha-hydroxyacids or polyhydroxy alpha-hydroxy acid such as glycolic acid, lactic acid, tartaric acid, gulonic acid and other carboxylic acids and their monomeric, polymeric, cyclic or acyclic derivatives; (iv) alpha-keto acids such as pyruvic acid, 2-oxopropanoic acid, 2-oxobutanoic acid, 2-oxopentanoic acid, and the like.

From about 0.1 to about 90%, preferably from about 1 to about 50%, and most preferably about 5 to about 20% of the oxa diacids can also be utilized for additional benefits in topical formulations containing one or more of the following:

(i)vitamins including, for example, enzyme co-factors such as vitamin B6, vitamin B12, vitamin D3, 1,25-dihydroxy vitamin D3, vitamin B1, vitamin B2, vitamin K, vitamin E, tocotrienols and their derivatives, nicotinic acid and its esters, pantothenic acid and it esters, panthenol, folic acid and its derivatives, choline, carnitine and substances without formal vitamin status or "pseudo vitamins" such as vitamin F or cis,cis-linoleic acid, vitamin M or pteroylglutamic acid, vitamins B10 and B11, sesame seed factor, termitin, penicin, insectine, hypomycin and mycoine, vitamin L or anthranilic acid, vitamin L2 or adenylthiomethylpentose, myoinositol or cis-1,2,3,5-trans-4-6-cyclohexanehexol and its esters, especially phytic acid, laetrile or 1-mandelo-nitrile-beta-glucuronic acid, amygdalin, vitamin B15 or pangamic acid, vitamin B13 or orotic acid, vitamine H3 or procaine hydrochloride, vitamin U or methyl-sulfonium salts of methionine, and pyrroloquinoline quinone;

(ii) antifungal agents including, for example, clotrimazole, ketoconazole, miconazole, naftifine, tolnaftate, amphotericin B, nystatin, 5-fluorocytosine, griseofulvin, haloprogin, of which tolnaftate, haloprogin and miconazole are most preferred;

(iii) self-tanning agents including, for example, as dihydroxyacetone and lawsone, of which dihydroxy-acetone is most preferred;

(iv) anti-mycobacterial agents such as erythromycin, tetracyclin and related compounds, especially doxycyclin and methacyclin, cephalosporins, penicillins, macrolides, peptide compounds such as novobiocin, vancomycin, oleandomycin paromomycin, leucomycine, amphomycin with macrolide molecules, quinolone derivatives and other compounds that interfere with bacterial cell wall synthesis, membrane function, RNA metabolism, purine, pyrimidine and protein synthesis, respiration or phosphorylation;

(v) topical analgesics such as lidocaine, benzocaine, butacaine, tetracaine, clove oil and eugenol, of which benzocaine and lidocaine are most preferred;

(vi) lipidic compounds essential for the skin's barrier function including, for example, ceramides, essential fatty acids and their esters, especially glycerides, ω-hydroxy fatty acids and their esters derived with alkanols through carboxylic hydroxyl or with, other fatty acids at the omega-hydroxyl, the latter type being most preferred, with phospholipids, cholesterol and its esters, such as cholesteryl hemisuccinate and cholesteryl phospate of which cholesterol phospate and essential fatty acids are most preferred, phytosterols, cholestanol and its derivatives. The lipidic compounds can be added to a topical composition either as singular molecular entities or as a complex mixture of lipids derived from either synthetic, animal or plant sources;

(vii) antiallergenic agents and H1 and/or H2 antihistamines, such as diphenylhydramine, clemizole, antazoline, thenaldine, phenyltoloxamine citrate, tricyclic antiallergenics such as ketotifene, dithiadene and 3-thienylsulfide of thiadene, H2-receptor blockers, especially burimamide, metiamide and cimetidien, cromolic acid and its salts;

(viii) the oxa-diacids can be used with topical anti-inflammatory agents that can reduce inflammation. These anti-inflammatory agents are used at concentrations from about 0.025% to 10%, preferably, 0.5–1%, with the concentration of the anti-inflammatory adjusted upward or downward depending upon the potency of the utilized agents. Examples of steroidal anti-inflammatories that can be used with oxa diacids include hydrocortisone, hydroxytriamcilone, alpha-methyl dexamethasone, dexamethasone phosphate, beclamethasone dipropionate, hydrocortisone valerate, hydrocortisone cyclopentylpropionate, prednisolone, and mixtures thereof, with the most preferred being prednisolone and hydrocortisone; and (ix) non-steroidal anti-inflammatories can also be employed, such as described in Rainsford, *Antiinflammatory and Anti-Rheumatic Drugs,* Vols. I–III, CRC Press, Boca Raton, Fla. (1985), and specific examples of suitable NSAID's including, for example, oxicams (e.g. piroxicam, isoxicam), fenamic acid derivatives, meclofenamic acid derivatives (e.g. sodium meclofenamate), flufenamic acid derivatives, mefenamic acid derivatives, propionic acid esters, such as ibuprofen, naproxen, benoxaprofen, flubiprofen, ketoprofen, suprofen, of which ibuprofen is most preferred; pyrazolidinediones, of which phenylbutazone is most preferred; acetic acid derivatives, such as diclofenac, fenclofenac, indomethacin, sulindac, of which indomethacin is most preferred; salicylic acid derivatives, such as, for example, asprin, disalacid, and benorylate, of which aspirin and disalacid are most preferred.

The compositions of the invention may also include safe anti-inflammatory products of natural origin shown to possess anti-inflammatory activity such as aloe vera extracts, extracts from genus Rubis (Rubia Cordifolia), extracts from genus Commiphom (Commiphora Mukul), willow bark, matricarria flowers, arnica flower, comfrey root, fenugreek seed and the like known to those skilled in the art.

Topical compositions of the invention can contain from about 0.1 to about 90%, preferably from about 1 to about 50%, and most preferably about 5 to about 20% of the oxa diacids in combination with antioxidants with phenolic hydroxy functions such as gallic acid derivataives (e.g. propyl gallate), bio-flavonoids (e.g. quercetin, rutin, daidzein, genistein), ferrulic acid derivatives (e.g. ethyl ferrulate, sodium ferrulate), 6-hydroxy-2,5,7, tetramethylchroman-2-carboxylic acid. The compositions may also contain effective concentrations of water soluble antioxidants such as uric acid, reductic acid, tannic acid, rosmarinic acid and catechins.

Also of benefit is a coformulation from about 0.1 to about 90%, preferably from about 1 to about 50%, and most preferably about 5 to about 20% of the oxa diacids with nitric oxide synthase inhibitors that reduce skin redness, vasodilation and inflammatory reactions, especially in response to electromagnetic and ionizing radiation or to the action of chemically or biochemically aggresive compounds. The nitric oxide synthase inhibitors can be added at concentrations from about 0.05% to 10%, most preferably from 1% to 3%, and selected from the group including guanidine derivatives, especially monoaminoguianidine and methylguanidine, L-arginine derivatives, especially $N^G$-nitro-L-arginine and its esters, $N^G$-monomethyl-L-arginine, 2-iminopipperidines and other 2-iminoazaheterocycles.

Other possible anti-oxidants that the composition may contain are those that have one or more thiol functions (—SH), in either reduced or non-reduced form, such as glutathione, lipoic acid, thioglycolic acid, and other sulfhydryl compounds. The levels of sulfhydryl anti-oxidants should not exceed 0.5% for cosmetic uses of the composition but may be higher for pharmaceutical uses as dictated by the considerations of efficacy. The composition may also include inorganic antioxidants such as sulfites, bisulfites, metabi-sulfite, or other inorganic salts and acids containing sulfur in oxidation state +4. The preferred level of inorganic sulfur-containing antioxidants is from about 0.01% to about 0.5% with the most preferred level between about 0.1% and about 0.4% by weight.

Compositions of the invention can also include from about 0.1 to about 90%, preferably from about 1 to about 50%, and most preferably about 5 to about 20% of the oxa diacids coformulated with about 0.025% to 5%, with 0.5%–2% preferred and with 0.5–1% most preferred, of compounds known to be electron spin-traps such as nitrones, N-tertbutyl-nitrone and a-(4-pyridyl-1-oxide)-N-tertbutyl-nitrone or other compounds known to form free radicals with half-life times of more than one minute.

From about 0.1 to about 90%, preferably from about 1 to about 50%, and most preferably about 5 to about 20% of the oxa diacids can also be used in compositions that contain insect repellents such as aliphatic, cyclic or aromatic amides, citronella oil, terpineol, cineole, neem oil and terephthalic acid and its esters. Other suitable insect repellents can be found in Technical Bulletin No. 1549 from the U.S. Department of Agriculture or in their Agricultural Handbook Nos. 69, 340 and 461.

The oxa diacid-containing topical compositions of the invention can also contain skin cooling compounds such as, by way of example, menthol, menthyl glycerol, asymmetrical carbonates, thiocarbonates and urethanes, N-substituted carboxamides, ureas or phosphine oxides such as described in *J. Cosmet. Chem.,* vol. 29, p. 185 (1978), menthyl lactate, and menthone glycerine acetal.

The general activity and mildness to skin of the present topical compositions can also be enhanced by neutralization to pH 3.5 to 7.0, most preferably from pH 3.7 to 5.6, with one or more amphoteric and pseudoamphoteric compounds such as glycine, alanine, valine, serine, thionine, methionine, leucine, asparagine, histidine, glutamic acid, glutamine, lysine, cystine, cystein, tryptophan, serine, phenylalanine, citrulline, creatine, proline, 3- or 4-hydroxyproline, 5-hydroxylysine, ornithine and its derivatives, 3-aminopropanoic acid and other aminocarboxylic acids, canavanine, canaline, homoarginine, taurine, aminoaldonic acids and aminosugars, aminouronic acid, aminoaldaric acid, deacetylated hyaluronic acid, hyalobiuronic acid, chondrosine, desulfated heparin, neuraminic or sialic acid, methionine sulfone, glycylglycine, chondroitin, D,L-sphingosine, sphingomyelin, ophidine, glucagon, homocarnosine, phosphatidyl serine, cocoamphoglycine, phosphatidyl ethanolamine, cysteinesulfinic acid, glutathione, amphoteric inorganic oxides, polyamidoamines, polyamidoamine-based dendrimers, sodium hydroxymethylglycinate and polyethylene amine.

The utility and mildness of the present topical compositions can also be enhanced by certain chelating agents incorporated into the composition at levels from about 0.01% to about 25% by weight, more preferably from about 0.5% to 10%, and most preferably from about 1% to about 5%. Suitable examples of chelating agents include those that have a high affinity for zinc, calcium, magnesium, iron and/or copper ions, such as ethylene-diamine-tetra-acetic acid, (ethylenedioxy)-diethylene-dinitrilo-tetra-acetic acid, salicylaldoxime, quinolinol, diaminocyclohexane-tetra-acetic acid, diethylene-triamino-penta-acetic acid, dimethylglyoxime, benzoin oxime, triethylenetetramine, desferrioxamine or mixtures thereof.

The present invention also includes methods by which these compounds can be used to address the aforementioned skin conditions. Such methods include topically applying an effective amount of one or more compound of Formula (I) to the affected skin areas, normally once or twice daily. Such methods also include topically applying a composition containing an effective amount of one or more compounds of Formula (I) in a physiologically acceptable vehicle to the affected skin areas, normally once or twice daily. The methods of the present invention include the topical application of the compounds of Formula (I) in concentrations of up to 100%, when such compounds are a liquid at ambient temperature (e.g. 3,6,9-trioxaundecanedioic acid), and when using the oxa compounds, for example, for skin peels or for softening hair.

The following examples are illustrative of the present invention and are not intended to limit the invention.

EXAMPLES

The compositions of the present invention are generally made into lotions, creams or gels for topical application.

EXAMPLE 1

Preparation of Oxa diacid Topical Compositions

In a suitable vessel, water, glycerin, propylene glycol Na$_2$EDTA and trioxaundecanoic acid are added and mixed together. Ammonium hydroxide is added to the vessel in increments to adjus pH to the desired range. This pH-adjusted phase is then heated to 170–175° F. Hydroxyethyl cellulose is next added with agitation until uniform to complete phase A.

For the lotion and cream, phase B is added to a suitable, second vessel, combined and heated to 170–175° F. Phase B is then added to phase A with sufficient mixing, again at 170–175° F. The batch is then cooled to 120° F. Phase C is added to the batch and mixed until uniform.

| Phase | | GEL | LOTION | CREAM |
|---|---|---|---|---|
| (A) | water | Q.S. | Q.S. | Q.S. |
| | glycerin | 5.00 | 3.00 | 5.00 |
| | propylene glycol | 3.00 | 3.00 | 3.00 |
| | disodium-EDTA | 0.10 | 0.10 | 0.10 |
| | 3,6,9-trioxa-undecanoic acid | 10.00 | 10.00 | 10.00 |
| | hydroxyethyl cellulose | 0.50 | 0.30 | 0.500 |
| | ammonium hydroxide (30%) | to pH 3.7–3.9 | to pH 3.7–3.9 | to pH 3.7–3.9 |
| (B) | octyl palmitate | — | 3.00 | 5.00 |
| | myristyl myristate | — | 3.00 | 5.00 |
| | glyceryl monostearate | — | 1.50 | 3.00 |
| | cetearyl alcohol & Ceteareth-20 | — | 3.00 | 5.00 |
| | methyl paraben | — | 0.20 | 0.20 |
| (C) | imidazolidilyl urea | 0.30 | 0.30 | 0.30 |

All numbers are expressed as percentages of total weight of composition except for pH ranges and Q.S. for balance with water.

Those skilled in the art will readily perceive possible vehicles other than lotions, creams or gels, after having the benefit of this disclosure.

Microscopic normalization of desquamation of the stratum corneum or macroscopic exfoliation of the epidermis are prerequisite activities for alleviating the skin conditions for which the present oxa diacid compounds and compositions are intended. The following example demonstrates, inter alia, the superior stratum corneum desquamatory activity provided by the present oxa diacid compositions.

EXAMPLE 2

Exfoliation Patch Test for Desguamatory Activity

In general, the exfoliation patch test procedure involves a 24-hour occlusive patching to a skin site. Skin gradings are conducted immediately, and 24 hours after, removal of the patch. The test focuses primarily on product effects on the stratum corneum and mainly on exfoliation.

A corneocyte removing activity sampling (a "CRAS") is taken following the visual grading at 24 hours after removal of the patch. A CRAS score is a quantitative measure of corneocyte desquamation and its calculation is based on the amount of corneocytes removed with each sampling.

A series of studies were conducted, the first of which showed that in a 1-day exfoliation CRAS assay, a 10 wt % 3,6,9-trioxaundecanedioic acid composition at pH 3.7 had superior exfoliating activity compared to a formulation containing 4 wt % glycolic acid at pH 3.8. This study examined the exfoliation properties of 10 wt % oxa diacid at low and high pH, and 5 wt % oxa diacid at low pH. The 4 wt % glycolic acid was included as a frame of reference. Table 1, below, provides a complete data summary as well as material identification.

TABLE 1

| | pH | CRAS |
|---|---|---|
| 5 wt-% oxa diacid | 3.7 | 2.58 |
| 10 wt % oxa diacid | 3.7 | 2.93 |
| 10 Wt % oxa diacid | 5.4 | 2.68 |
| 4 wt % glycolic acid | 3.8 | 2.80 |

No significant irritation was observed with any sanple. In all of the various comparisons, the 10% oxa diacid low pH sample was consistently better and exhibited meaningful exfoliation activity.

The next study in the series re-confirmed that a composition with 10 wt % of 3,6,9-trioxaundecanedioic acid has an exfoliating activity superior to that of a 4 wt % glycolic acid formulation. At the same time, the 3,6,9-trioxaundecanedioic acid composition was also milder to the skin than the glycolic acid. It is to be noted that, on a molar basis, the concentration of "acid" in a 10% 3,6,9-trioxaundecanedioic acid composition is lower than that in a 4% glycolic acid formula. Coupled with the clinical results presented herein, this indicates that the intrinsic exfoliating activity of 3,6,9-trioxaundecanedioic acid is significantly higher than that of glycolic acid.

The second study was performed to confirm the results observed with the 10 wt % oxa diacid compositions at pH 3.7. Table 2, below, provides a data summary and material identification for the second study.

TABLE 2

|  | pH | PII | CRAS | Previous CRAS |
|---|---|---|---|---|
| 10% oxa diacid | 3.7 | 0.13 | 3.23 | 2.93 |
| 10% oxa diacid | 3.74 | 0.18 | 3.33 | — |
| 4% glycolic acid | 3.7 | 0.23 | 3.05 | 2.80 |

No significant irritation was observed with any of the sampled participants, but use of the oxa diacids did provide lower irritation index (PII) scores in comparison to both the glycolic acid and vehicle. The results confirmed what was observed in the exfoliation assay of Example 2.

EXAMPLE 3

Cream for Hyperpigmented Spots

This example illustrates a cream that can be prepared and used to reduce appearance of hyper-pigmentation spots on the skin of hands.

|  | W/W % |
|---|---|
| isopropyl myristate | 3.0 |
| polyethylene glycol (1000) monostearate | 5.0 |
| palmitic acid | 10.0 |
| 3,6,9,12-tetraoxatetradecanedioic acid | 10.0 |
| glycerine. | 3.0 |
| polyethylene glycol (300) monostearate | 5.0 |
| methyl paraben | 0.2 |
| magnesium ascorbyl phosphate | 2.0 |
| water | 60.0 |
| perfume & color | to 100.0 |
| triethanolamine | to pH 4.0 |

All numbers are expressed as percentages of total weight of compositions except for reference to pH.

EXAMPLE 4

Cream for Dry Skin, Ichthyosis and Hyperkeratoses

This example illustrates a silicone cream that can be prepared and used to treat dry skin, ichthyosis and hyperkeratoses according to the present invention.

|  | W/W % |
|---|---|
| Phase A |  |
| laurylmethicone copolyol | 2.0 |
| mineral oil | 1.0 |
| lanolin | 1.5 |
| sunflower or soybean oil | 10.0 |
| cyclomethicone | 6.0 |
| oil soluble rosmary extract | 2.0 |
| Phase B |  |
| sodium iodide | 2.0 |
| 3,6,9-trioxaundecandioic acid | 9.0 |
| 3,6,9,12,15-pentaoxaheptadecanedioic acid | 1.0 |
| sodium hydroxymethyl glycinate | 0.5 |
| demineralized water | to 100.0 |
| sodium hydroxymethyl glycinate | to pH 3.8 |

All numbers are expressed as percentages of total weight of composition except for the reference to pH.

EXAMPLE 5

Silicone Gel

This example illustrates a water-in-silicone gel composition.

|  | W/W % |
|---|---|
| Phase A |  |
| dimethiconol | 10.0 |
| dimethicone copolyol | 10.0 |
| cyclomethicone | 5.0 |
| Phase B |  |
| 3,6,9-trioxaundecanedioic acid | 8.0 |
| glycerine | 20.0 |
| demineralized water | to 100.0 |
| triethanolamine | to pH 4.0 |

All numbers are expressed as percentages of total weight of composition except for the reference to pH.

EXAMPLE 6

Cream for Acne, Skin Blemishes and Age Spots

This example illustrates a face cream that can be used to treat acne, skin blemishes and age spots.

|  | W/W % |
|---|---|
| Phase A |  |
| oleic acid | 1.0 |
| stearic acid | 17.0 |
| polyoxyethylene (20 propylene glycol monostrearate) | 10.0 |
| retinol | 0.1 |
| Phase B |  |
| glycerine | 5.0 |
| 2-pyrollidone-5-carboxylic acid | 5.0 |
| 3,6,9-trioxaundecanedioic acid | 7.5 |
| 3,6,9,12-tetraoxatetradecanedioic acid | 2.5 |
| lactic acid | 3.0 |
| demineralized water | to 100.0 |
| ammonium hydroxide | to pH 4.2 |

All numbers are expressed as percentages of-total composition except for the reference to pH.

Various modifications and alterations to the present invention may be appreciated based on a review of this disclosure. These changes and additions are intended to be within the scope and spirit of this invention as defined by the following claims.

What is claimed is:

1. A topical composition comprising:
a suitable topical vehicle, a compound of Formula I:

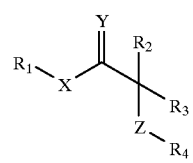

(I)

wherein $R_4$ is $(CR_5R_6—CR_7R_8—X_1)_n—CR_9R_{10}—C(=X_2)X_3R_{11}$, n is an integer from 1 to 18; $R_1$, $R_2$, $R_3$, $R_5$, $R_6$, $R_7$, $R_8$, $R_9$, $R_{10}$ and $R_{11}$, are independently, hydrogen or non-hydrogen substituents; and X, $X_1$, $X_2$, $X_3$, Y and Z, are independently, O, NH, or S; and
a component selected from the group consisting of estriol, estradiol, estrone, conjugated estrogens, alpha-hydroxy acids, alpha-keto acids, sunscreens, dihydroxyacetone, lawsone, ceramides, retinol, antioxidants, skin cooling compounds, and a mixture thereof.

2. The topical composition of claim 1, wherein the component is the retinol.

3. The topical composition of claim 1, wherein the component is the alpha-hydroxy acid.

4. The topical composition of claim 3, wherein the alpha-hydroxy acid is selected from the group consisting of glycolic acid, lactic acid, tartaric acid, gulonic acid, and a mixture thereof.

5. The topical composition of claim 3, wherein the alpha-hydroxy acid is selected from group consisting of glycolic acid, lactic acid, and a mixture thereof.

6. The topical composition of claim 1, wherein the component is the sunscreen.

7. The topical composition of claim 6, wherein the sunscreen is selected from the group consisting of titanium dioxide, cinnamic acid derivatives, butylmethoxydibenzoylmethane, and a mixture thereof.

8. The topical composition of claim 7, wherein the sunscreen is the butylmethoxydibenzoylmethane.

9. The topical composition of claim 7, wherein the sunscreen is the cinnamic acid derivative.

10. The topical composition of claim 7, wherein the sunscreen is the titanium dioxide.

11. The topical composition of claim 1, wherein the alpha-keto acid is selected from the group consisting of pyruvic acid, 2-oxopropanoic acid, 2-oxobutanoic acid, 2-oxopentanoic acid, and a mixture thereof.

12. The topical composition of claim 1, wherein the component is the mixture.

13. The topical composition of claim 12, wherein the mixture comprises the retinol and the alpha-hydroxy acid.

14. The topical composition of claim 13, wherein the alpha-hydroxy acid is selected from the group consisting of glycolic acid, lactic acid, and a mixture thereof.

15. The topical composition of claim 1, wherein the skin cooling compound is selected from the group consisting of menthol, menthyl glycerol, asymmetrical carbonates, thiocarbonates, urethanes, N-substituted carboxamides, urea, phosphine oxides, menthyl lactate, menthone glycerol acetal, and a mixture thereof.

16. The composition of claim 1, wherein the component is selected from the group consisting of dihydroxyacetone, lawsone, and a mixture thereof.

17. The composition of claim 1, wherein the component is selected from the group consisting of dihydroxyacetone, lawsone, and a mixture thereof.

18. A method of treating skin conditions caused by, accompanied with or exacerbated by abnormal desquamation, comprising the step of applying to said skin condition an effective amount of topical composition, said topical composition comprising:

a topical vehicle;

a compound of Formula I:

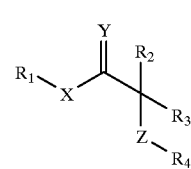

(I)

wherein $R_4$ is $(CR_5R_6-CR_7R_8-X_1)_n-CR_9R_{10}-C(=X_2)X_3R_{11}$, n is an integer from 1 to 18; $R_1$, $R_2$, $R_3$, $R_5$, $R_6$, $R_7$, $R_8$, $R_9$, $R_{10}$ and $R_{11}$, are independently, hydrogen or non-hydrogen substituents; and X, $X_1$, $X_2$, $X_3$, Y and Z, are independently, O, NH, or S; and a component selected from the group consisting of estriol, estradiol, estrone, conjugated estrogens, alpha-hydroxy acids, alpha-keto acids, sunscreens, dihydroxyacetone, lawsone, ceramides, retinol, antioxidants, skin cooling compounds, and a mixture thereof.

19. The method of claim 18, wherein the component is the retinol.

20. The method of claim 18, wherein the component is the alpha-hydroxy acid.

21. The method of claim 20, wherein the alpha-hydroxy acid is selected from the group consisting of glycolic acid, lactic acid, tartaric acid, gulonic acid, and a mixture thereof.

22. The method of claim 20, wherein the alpha-hydroxy acid is selected from group consisting of glycolic acid, lactic acid, and a mixture thereof.

23. The method of claim 18, wherein the component is the sunscreen.

24. The method of 23, wherein the sunscreen is selected from the group consisting of titanium dioxide, cinnamic acid derivatives, butylmethoxydibenzoylmethane, and a mixture thereof.

25. The method of claim 24, wherein the sunscreen is the butylmethoxydibenzoylmethane.

26. The method of claim 24, wherein the sunscreen is the cinnamic acid derivative.

27. The method of claim 24, wherein the sunscreen is titanium dioxide.

28. The method of claim 18, wherein the alpha-keto acid is selected from the group consisting of pyruvic acid, 2-oxopropanoic acid, 2-oxobutanoic acid, 2-oxopentanoic acid, and a mixture thereof.

29. The method of claim 18, wherein the component is the mixture.

30. The method of claim 29, wherein the mixture comprises the retinol and the alpha-hydroxy acid.

31. The method of claim 30, wherein the alpha-hydroxy acid is selected from the group consisting of glycolic acid, lactic acid, and a mixture thereof.

32. The method of claim 18, wherein the skin cooling compound is selected from the group consisting of menthol, menthyl glycerol, asymmetrical carbonates, thiocarbonates, urethanes, N-substituted carboxamides, urea, phosphine oxides, menthyl lactate, menthone glycerol acetal, and a mixture thereof.

* * * * *